United States Patent
Jaisankar et al.

(10) Patent No.: US 10,590,116 B2
(45) Date of Patent: Mar. 17, 2020

(54) 3-INDOLYL FURANOIDS AS INHIBITORS OF MATRIX METALLOPROTEINASE-9 FOR PREVENTION OF GASTRIC ULCER AND OTHER INFLAMMATORY DISEASES

(71) Applicant: Council of Scientific & Industrial Research, New Delhi (IN)

(72) Inventors: Parasuraman Jaisankar, West Bengal (IN); Snehasikta Swarnakar, West Bengal (IN); Sourav Chatterjee, West Bengal (IN); Sugreev Verma, West Bengal (IN); Madhumita Mandal, West Bengal (IN); Susri Ray Chaudhuri, West Bengal (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/897,688

(22) Filed: Feb. 15, 2018

(65) Prior Publication Data
US 2018/0230135 A1 Aug. 16, 2018

(30) Foreign Application Priority Data
Feb. 15, 2017 (IN) .............................. 201711005308

(51) Int. Cl.
*C07D 405/04* (2006.01)
*A61K 31/404* (2006.01)
*A61P 1/04* (2006.01)
*A61K 9/00* (2006.01)

(52) U.S. Cl.
CPC .......... *C07D 405/04* (2013.01); *A61K 9/0019* (2013.01); *A61K 9/0053* (2013.01); *A61K 31/404* (2013.01); *A61P 1/04* (2018.01)

(58) Field of Classification Search
CPC .................................................. C07D 405/04
See application file for complete search history.

(56) References Cited

PUBLICATIONS

Blay et al. (Tetrahedron, 2009, 65(45), pp. 9264-9270).*
Omar Kujan et al., "An Unusual Side Effect of Ibuprofen Post Dental Therapy: Increased Erectile and Libido Activity", J Int Oral Health, 2014, vol. 6(6), pp. 94-95.
Hamed Laroui et al., "Targeting Intestinal Inflammation With CD98 siRNA/PEI-loaded Nanoparticles", Molecular Therapy, 2014, vol. 22 No. 1, pp. 69-80.
Janelle L. Lauer-Fields et al., "Selective Modulation of Matrix Metalloproteinase 9 (MMP-9) Functions via Exosite Inhibition", J. Biol. Chem., 2008, Vo. 283, No. 29, pp. 20087-20095.
Shane O'Sullivan et al., "Nitric oxide-matrix metaloproteinase-9 interactions: Biological and pharmacological significance, NO and MMP-9 interactions", Biochimica et Biophysica Acta, 2014, vol. 1843, pp. 603-617.
Netta Sela-Passwell et al., "Structural and functional bases for allosteric control of MMP activities: Can it pave the path for selective inhibition?", Biochimica et Biophysica Acta, 2010, vol. 1803, pp. 29-38.
C.K.S. Ong et al., "An Evidence-Based Update on Nonsteroidal Anti-Inflammatory Drugs", Clinical Medicine & Research, 2007, vol. 5, No. 1, pp. 19-34.
Snehasikta Swarnakar et al., "Curcumin Regulates Expression and Activity of Matrix Metalloproteinases 9 and 2 during Prevention and Healing of Indomethacin-induced Gastric Ulcer", J. Biol. Chem., 2005, vol. 280, No. 10, pp. 9409-9415.
Arpit Tandon et al., "Structural insights into the binding of MMP9 inhibitors", Bioinformation, 2011, vol. 5, Issue 8, pp. 310-314.

* cited by examiner

*Primary Examiner* — Susanna Moore
(74) *Attorney, Agent, or Firm* — Dinsmore & Shohl, LLP

(57) ABSTRACT

Disclosed are 3-indolyl furanoid compounds which are useful as potent anti-inflammatory agents and prevent gastric ulcer by inhibiting matrix metalloproteinase-9 (MMP-9) expression in gastric mucosal layer. For example, disclosed is a compound of formula 1, Formula 1

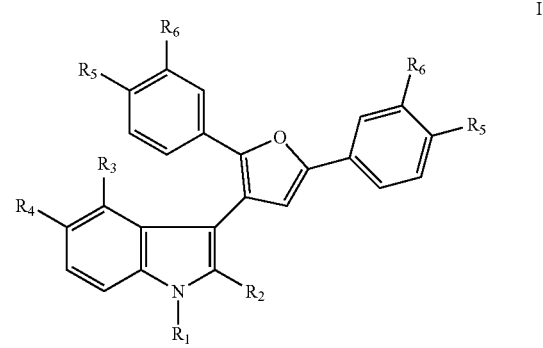

wherein: $R_1$ to $R_6$ is selected from H, OH, $CH_3$, $OCH_3$, Br, Cl, Ph or o-$OHC_6H_4$, $OCH_2$—CH=$CH_2$, or $OCH_2CH_2CH_3$, and $R_1$ to $R_6$ is having at least one substituent with alkyl, aryl and heteroaryl groups other than H, wherein the carbon in alkyl, aryl and heteroaryl is in the range of C1 to C8. Various embodiments relate to representative compounds of Formula 1 and method of preparation thereof. Further embodiments relates to the use of representative compounds of Formula 1 in treating diseases associated with gastric ulcer and other inflammatory diseases. A noted feature of an embodiment is the IC50 value of 50 μM of one of the 3-indolyl furanoids.

11 Claims, 7 Drawing Sheets

Scheme 1

Scheme 2

3-INDOLYL FURANOIDS AS INHIBITORS OF MATRIX METALLOPROTEINASE-9 FOR PREVENTION OF GASTRIC ULCER AND OTHER INFLAMMATORY DISEASES

TECHNICAL FIELD

The present disclosure generally relates to 3-indolyl furanoid compounds which act as potent anti-inflammatory agents and prevent gastric ulcer by inhibiting matrix metalloproteinase-9 (MMP-9) expression in gastric mucosal layer. Particular embodiments of the present invention relate to a compound of Formula 1, Formula 1

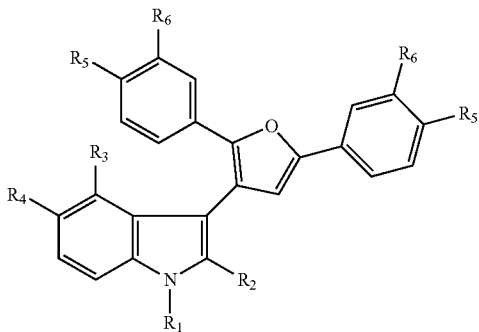

wherein
$R_1$ to $R_6$ is selected from H, OH, $CH_3$, $OCH_3$, Br, Cl, Ph or o-OHC$_6$H$_4$, $OCH_2$—CH=$CH_2$, or $OCH_2CH_2CH_3$
and
$R_1$ to $R_6$ is having at least one substituent with alkyl, aryl and heteroaryl groups other than H, wherein the carbon in alkyl, aryl and heteroaryl is in the range of C1 to C8.
Even more particularly, certain embodiments of the present invention relate to representative compounds of Formula 1 and method of preparation thereof. Further, various embodiments of the present invention relate to the use of representative compounds of Formula 1 in treating diseases associated with gastric ulcer and other inflammatory diseases.

BACKGROUND

Gastric ulcer is an open sore or raw area in the lining of the stomach. The most common cause of this disease is the infection of the stomach by bacteria called *Helicobacter pylori*. Most people with gastric ulcer have these bacteria in their digestive system. Yet many people having these bacteria in their stomach do not develop an ulcer. There are several exogenous factors such as excessive alcohol consumption, regular intake of non-steroidal anti-inflammatory drugs (NSAID), cigarette smoking, tobacco chewing, radiation treatment, etc., which lead to hyper-secretion of hydrochloric acid and pepsin followed by hyper-activation of leukotrienes and generation of reactive oxygen species (ROS), causing damage of gastric mucosal layer and initiating ulceration. Then *Helicobacter pylori*, an opportunistic bacterium, act on the damaged mucosal layer and aggravate the risk of gastric ulcer.

The molecular aspect of gastric ulcer is the pathogenesis which is related to the reduction of mucosal blood flow or a break down in other normal mucosal defence mechanisms in conjunction with injurious effects of acids and malfunctioning or deregulation of various proteases including MMPs in the gastric mucosa.

Small molecule inhibitors of MMPs are known to protect inflammation but give rise to gastric ulcer as severe side effect. See, References 1-3. Recent reports on the development of resistance to such compounds emphasize the need for further therapeutic development to control gastric inflammation. See, References 4, 5. It has been reported that indomethacin is a nonsteroidal anti-inflammatory drug with potent antipyretic, analgesic, and anti-inflammatory activity. It has been effectively used in the management of mild-to-moderate pain since the mid-1960s. It is commonly prescribed for the relief of acute gouty arthritis pain, but has demonstrated efficacy in the treatment of various other painful conditions (Postgrad Med., 2014, 126, 4, 92). Melatonin also belongs to NSAIDs which binds to the catalytic domain of MMP-9 and interacts with the key active site residues of this protease. Understanding the comprehensive molecular structure and the conformational changes of MMP-9 in its inhibited state may aid in the rational design of anti-ulcer/anti-inflammatory drugs. See, References 6-8.

Modern therapeutics for the treatment of gastric ulcer and other inflammatory diseases involve the use of antibiotics, such as amoxicillin, tetracycline, and metronidazole/clarithromycin, along with ranitidine, bismuth citrate and bismuth subsalicylate. Gastric acid suppression by $H_2$ blockers or proton pump inhibitor in conjunction with the antibiotics helps alleviate ulcer-related symptoms (i.e., abdominal pain, nausea) and heals gastric mucosal inflammation by enhancing the efficacy of antibiotics against *H. pylori* at the gastric mucosal surface. Currently, eight *H. pylori* treatment regimens are approved by the Food and Drug Administration (FDA). However, several other combinations have been used successfully. Antibiotic resistance and patient noncompliance are the two major reasons for treatment failure.

SUMMARY

Various embodiments of the present invention relate to the development of 3-indolyl furanoid analogues as potent inhibitors of MMP-9 to prevent gastric ulcer and other inflammatory diseases. The inventors have unravelled the anti-inflammatory activities of 3-indolyl furanoid analogues along with their anti-ulcerous property. Their antioxidant properties and significant activity to prevent gastric ulceration in vivo in mice model have been found to occur through depletion of lipid peroxidation, and via bringing superoxide dismutase activity and MMP-9 inhibitory activity to normalcy in mouse gastric tissues.

Various embodiments of the present invention provide new 3-indolyl furanoid compounds of formula 1, which act as potent anti-inflammatory agents and prevent gastric ulcer by inhibiting matrix metalloproteinase-9 (MMP-9) expression in gastric mucosal layer. Formula 1 is as follows:

Formula 1

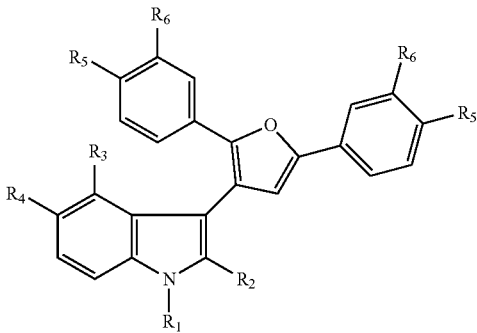

wherein
R₁ to R₆ is selected from H, OH, CH₃, OCH₃, Br, Cl, Ph or o-OHC₆H₄, OCH₂—CH═CH₂, or OCH₂CH₂CH₃
and
R₁ to R₆ is having at least one substituent with alkyl, aryl and heteroaryl groups other than H, wherein the carbon in alkyl, aryl and heteroaryl is in the range of C1 to C8.

Another embodiment provides a process for preparation of compounds of formula 1.

Still another embodiment is directed to the development of small molecule inhibitors of protease, especially metalloprotease which are associated with gastric ulcer and other inflammatory diseases.

In still another embodiment efforts to understand the interaction of compound 5 with active site of MMP-9 through molecular docking and in vivo experiments have been made and realized.

Yet another embodiment provides a method of treating diseases associated with over expression of metalloprotease activity by administrating therapeutically effective dose of compounds of formula 1.

Still another embodiment relates to the treatment of gastric ulcer and other inflammatory diseases.

According to another embodiment of the present invention, disclosed is a method of treating diseases associated with over expression of metalloprotease activity by administrating therapeutically effective dose of compounds of general formula 1

Formula 1

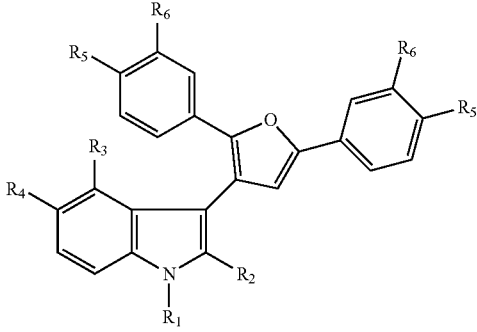

wherein
R₁ to R₆ is selected from H, OH, CH₃, OCH₃, Br, Cl, Ph or o-OHC₆H₄, OCH₂—CH═CH₂, or OCH₂CH₂CH₃
and
R₁ to R₆ is having at least one substituent with alkyl, aryl and heteroaryl groups other than H, wherein the carbon in alkyl, aryl and heteroaryl is in the range of C1 to C8.

In an embodiment of the present invention, the diseases are associated with overexpression of matrix metalloprotease-9.

In another embodiment of the present invention, the diseases are selected from the group consisting of gastric ulcer and other inflammatory diseases.

In yet another embodiment of the present invention, the treatment of gastric ulcer is by inhibition of matrix metalloproteinase-9 (MMP-9) pathway.

In a preferred embodiment of the present invention, the treatment of other inflammatory diseases is by inhibition of matrix metalloproteinase-9 (MMP-9) pathway.

In an embodiment of the present invention, a compound of formula 1:

Formula 1

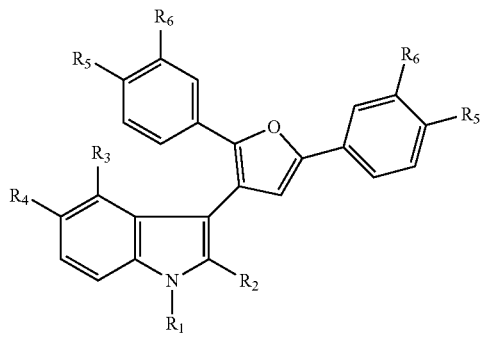

wherein
R₁ to R₆ is selected from H, OH, CH₃, OCH₃, Br, Cl, Ph or o-OHC₆H₄, OCH₂—CH═CH₂, or OCH₂CH₂CH₃
and
R₁ to R₆ is having at least one substituent with alkyl, aryl and heteroaryl groups other than H, wherein the carbon in alkyl, aryl and heteroaryl is in the range of C1 to C8.

In still another embodiment of the present invention, the compound of Formula 1 are selected from the group consisting of:
(1) 3-(2,5-diphenylfuran-3-yl)-1H-indol-5-ol;
(2) 3-(2,5-diphenylfuran-3-yl)-5-methoxy-1H-indole;
(3) 5-(allyloxy)-3-(2,5-diphenylfuran-3-yl)-1H-indole;
(4) 3-(2,5-diphenylfuran-3-yl)-5-propoxy-1H-indole;
(5) 4-methoxy-3-(2,5-diphenylfuran-3-yl)-1H-indole;
(6) 4,5-dimethoxy-3-(2,5-diphenylfuran-3-yl)-1H-indole;
(7) 4-bromo-3-(2,5-diphenylfuran-3-yl)-1H-indole;
(8) 2-phenyl-3-(2,5-diphenylfuran-3-yl)-1H-indole;
(9) 3-(2,5-diphenylfuran-3-yl)-2-(2-hydroxyphenyl)-1H-indole;
(10) 3-(2,5-diphenylfuran-3-yl)-2-methyl-1H-indole;
(11) 1,2-dimethyl-3-(2,5-diphenylfuran-3-yl)-1H-indole;
(12) 4-methoxy-1-methyl-3-(2,5-diphenylfuran-3-yl)-1H-indole;
(13) 3-[2,5-bis(4-chlorophenyl)furan-3-yl]-2-phenyl-1H-indole;
(14) 3-[2,5-bis(4-chloro-3-methylphenyl)furan-3-yl]-2-phenyl-1H-indole;

(15) 2-phenyl-3-(2,5-di-p-tolylfuran-3-yl)-1H-indole; and
(16) 3-[2,5-bis(4-bromophenyl)furan-3-yl]-2-phenyl-1H-indole.

In another embodiment of the present invention, the method of treating of gastric ulcer is by administrating an effective amount of 3-indolyl furanoid by inhibiting MMP-9 activity.

In yet another embodiment of the present invention, the method of treating other inflammatory disease is by administrating an effective amount of 3-indolyl furanoid by inhibiting MMP-9 activity.

In a preferred embodiment of the present invention, the pharmaceutical composition comprising the compound of formula 1 as claimed in claim 1, wherein the compound is in the range of 0.1 to 99% along with additives.

In yet another embodiment of the present invention, wherein the additives is selected from the group consisting of fillers, antioxidants, dispersants, emulsifiers, flavours, preservatives, solublizers and colorants.

In a preferred embodiment of the present invention, wherein the composition is in the form of tablets and capsules.

In another embodiment of the present invention, wherein the compound is in the range of 30 to 95% for tablets and 3-50% for capsules.

In another preferred embodiment of the present invention, the pharmaceutical composition comprises an effective amount of 3-indolyl furanoid.

In still another preferred embodiment of the present invention, the 3-indolyl furanoid are synthetically prepared.

In another embodiment of the present invention, said pharmaceutical composition is administered through oral route.

In yet another embodiment of the present invention, said pharmaceutical composition administered intraperitoneally.

In still another embodiment of the present invention, said pharmaceutical composition is administered orally at a dose level ranging between 10 to 50 mg per kg body weight.

In yet another embodiment of the present invention, said pharmaceutical composition administered intraperitoneally at a dose level ranging between 5 to 25 mg per kg body weight.

In a preferred embodiment of the present invention, wherein $IC_{50}$ value for in vitro activity of compound of formula 1 against AGS cells is ~50 µM.

In another preferred embodiment of the present invention, there is provided a method of treating of gastric ulcer by administrating an effective amount of the pharmaceutical composition.

In still another preferred embodiment of the present invention, there is provided a method of treating of other inflammatory diseases by administrating an effective amount of the pharmaceutical composition.

In another preferred embodiment of the present invention, the present invention involves formulation of new small molecule inhibitors whose biological significance has never been disclosed.

In still another preferred embodiment of the present invention, the synthesized chemical compounds namely 3-indolyl furanoids of Formula 1 are the inhibitors of protease, in particularly metalloproteases which are associated with gastric ulcer and other inflammatory diseases.

In another embodiment of the present invention, the mechanistic study of gastric ulcer and other inflammatory disease prevention by chemical compositions of new 3-indolyl furanoids suggest that the synthetic inhibitors functions through matrix metalloprotease-9 (MMP-9) pathway.

In yet another embodiment of the present invention, synthetically formulated inhibitors of 3-indolyl furanoids, compound 5 (table 1, entry 5) shows most promising anti-ulcer efficacy having $IC_{50}$=50 µM (FIG. 4). It is non-toxic and has better bio availability.

In still another preferred embodiment of the present invention, the development of 3-indolyl furanoids which act as potent anti-inflammatory agents and prevent gastric ulcer by inhibiting the expression of matrix metalloproteinase-9 (MMP-9) in gastric mucosal layer. The formulation of compound 5 (table 1, entry 5) was found to have potent anti-inflammatory activity and anti-ulcer activity with $IC_{50}$ value of 50 µM (FIG. 4). This present invention regards to structural as well as proposed activity of 3-indolyl furanoids and their mechanism of action against matrix metalloproteinase-9 (MMP-9) in gastric mucosal layer.

In still another preferred embodiment of the present invention, there is provided a pharmaceutical composition for the treatment of ulcer and inflammation, said composition comprising an effective amount of synthetically derived new 3-indolyl furanoids of Formula 1 and pharmaceutically acceptable additives. Formula 1 is as follows:

Formula 1

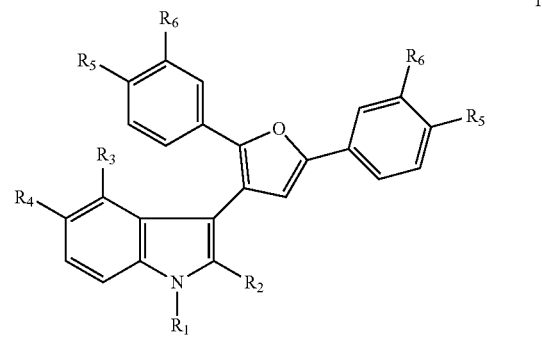

wherein
$R_1$ to $R_6$ is selected from H, OH, $CH_3$, $OCH_3$, Br, Cl, Ph or o-$OHC_6H_4$, $OCH_2$—CH=$CH_2$, or $OCH_2CH_2CH_3$
and
$R_1$ to $R_6$ is having at least one substituent with alkyl, aryl and heteroaryl groups other than H, wherein the carbon in alkyl, aryl and heteroaryl is in the range of C1 to C8.

DETAILED DESCRIPTION

Figure 1A:
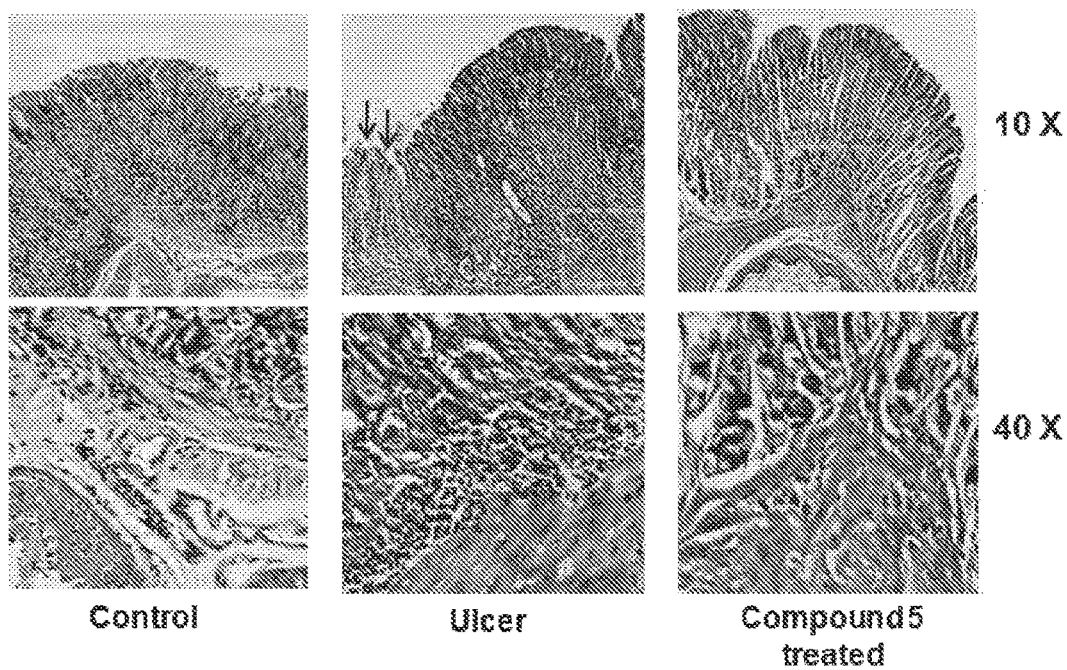
FIG. 1A and FIG. 1B shows compound 5 prevents indomethacin induced gastric injury with Haematoxylin-eosin staining (FIG. 1A) or with TUNEL assay of gastric tissue sections (FIG. 1B).

Various embodiments of the present invention relate to 3-indolyl furanoid compounds which act as potent anti-inflammatory agents and prevent gastric ulcer by inhibiting matrix metalloproteinase-9 (MMP-9) expression in gastric mucosal layer. Particularly, various embodiments the present invention relate to a compound of formula 1, Formula 1

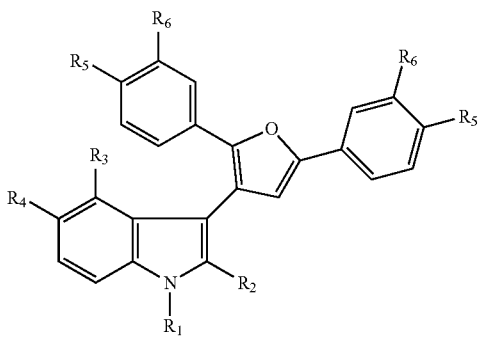

wherein
$R_1$ to $R_6$ is selected from H, OH, $CH_3$, $OCH_3$, Br, Cl, Ph or o-$OHC_6H_4$, $OCH_2$—CH=$CH_2$, or $OCH_2CH_2CH_3$
and
$R_1$ to $R_6$ is having at least one substituent with alkyl, aryl and heteroaryl groups other than H, wherein the carbon in alkyl, aryl and heteroaryl is in the range of C1 to C8.

Various embodiments of the present invention relate to representative compounds of Formula 1 and method of preparation thereof. Further embodiments of the present invention relate to the use of representative compounds of Formula 1 in treating diseases associated with gastric ulcer and other inflammatory diseases. The inventors have discovered that a promising feature of an embodiment of this invention is the IC50 value of 50 μM of one of the 3-indolyl furanoids.

Various embodiments of the present invention relate to the development of 3-indolyl furanoids which act as potent anti-inflammatory agents and prevent gastric ulcer. The inventors have developed 3-indolyl furanoids, particularly compound 5 in an embodiment which was found to have potent anti-inflammatory and anti-ulcerous activity with $IC_{50}$ value of 50 μM. Moreover, the inventors have discovered that 3-indolyl furanoids inhibit the expression of matrix metalloproteinase-9 (MMP-9) in gastric mucosal layer to prevent gastric ulcer.

Further, various embodiments of the present invention relate to the field of drug discovery, specifically of small molecule inhibitors for the treatment of gastric ulcer and other inflammatory diseases.

In summary, the embodiments of this invention are based upon a perfect combination of synthetic chemistry and advanced biology and represents the modern aspects of chemical biology for drug discovery.

Synthesis of 3-Indolyl Furanoids

In an exemplary embodiment, the inventors synthesized a series of 3-furanyl indole analogues (Table 1) via regioselective one-pot synthesis by Friedel-Crafts alkylation followed by Paal-Knorr cyclization. The synthetic route for the targeted, 3-indolyl furanoid derivatives (compounds 1-16) is shown in Scheme 1. The procedure involves the introduction in of a 1,4-dicarbonyl moiety on the indole framework via a Friedel-Crafts alkylation with (E)-1,4-diaryl-2-buten-1,4-diones (2), which could be transformed into furan rings via a Paal-Knorr cyclization by using p-TsOH as catalyst to yield the desired compounds 1-16 (Scheme 1). The inventors have also studied the reaction conditions using different catalysts such as $CH_3SO_3H$, $Cu(OTf)_2$, $CuCl_2$, $CH_3COOH$ and HCl under identical reaction condition. Among the various catalysts and solvents screened, p-TsOH in dichloromethane appeared to be a better catalytic system for synthesis of 3-indolyl furanoid derivatives (compounds 1-16). Accordingly, 3-(2,5-diphenylfuran-3-yl)-1H-indol-5-ol (compound 1) was obtained with 71% isolated yield upon reaction between indole (1a) and (E)-1,4-diphenyl-2-buten-1,4-dione (2a) in dichloromethane at 60° C. in the presence of 5 mol % p-TsOH as catalyst (Table 1, Sl. No. 1). In all cases the corresponding 3-indolyl furanoid derivatives (compounds 1-16) were obtained in good yields (62-85%).

TABLE 1

Synthesized analogues of 3-(2,5-diphenylfuran-3-yl)-1H-indole (compounds 1-16)

| Compound Sl. No. | $R_1$ | $R_2$ | $R_3$ | $R_4$ | $R_5$ | $R_6$ | Time (h) | Isolated Yield (%) |
|---|---|---|---|---|---|---|---|---|
| 1 | H | H | H | OH | H | H | 2 | 71 |
| 2 | H | H | H | OMe | H | H | 1.5 | 80 |
| 3 | H | H | H | O-allyl | H | H | 5 | 73 |
| 4 | H | H | H | O-propyl | H | H | 6 | 62 |
| 5 | H | H | OMe | H | H | H | 1 | 85 |
| 6 | H | H | OMe | OMe | H | H | 1.5 | 78 |
| 7 | H | H | Br | H | H | H | 2 | 75 |
| 8 | H | Ph | H | H | H | H | 1 | 85 |
| 9 | H | o-$OHC_6H_4$ | H | H | H | H | 1 | 82 |

TABLE 1-continued

Synthesized analogues of 3-(2,5-diphenylfuran-3-yl)-1H-indole
(compounds 1-16)

| Compound Sl. No. | $R_1$ | $R_2$ | $R_3$ | $R_4$ | $R_5$ | $R_6$ | Time (h) | Isolated Yield (%) |
|---|---|---|---|---|---|---|---|---|
| 10 | H | Me | H | H | H | H | 1 | 84 |
| 11 | Me | Me | H | H | H | H | 2 | 80 |
| 12 | Me | H | OMe | H | H | H | 1 | 82 |
| 13 | H | Ph | H | H | Cl | H | 1 | 80 |
| 14 | H | Ph | H | H | Cl | Me | 1 | 82 |
| 15 | H | Ph | H | H | Me | H | 1 | 80 |
| 16 | H | Ph | H | H | Br | H | 2 | 70 |

All the structurally proposed new compounds (1-16) have been characterized from their NMR and mass spectral data. In addition, the structure of compound 5 was also confirmed by X-ray single crystal analysis.

In another embodiment of the present invention, the structural formulae of the representative compounds are:

Compound 1

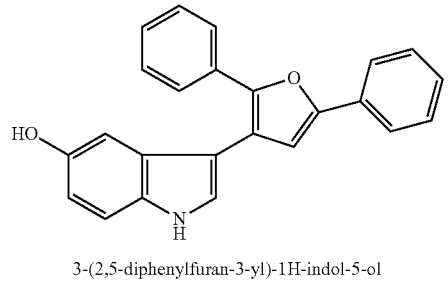

3-(2,5-diphenylfuran-3-yl)-1H-indol-5-ol

Compound 2

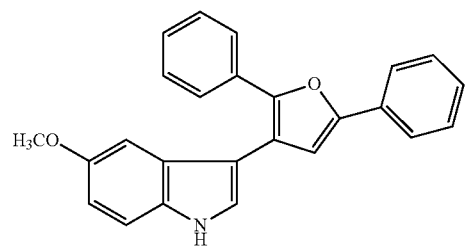

5-methoxy-3-(2,5-diphenylfuran-3-yl)-1H-indole

Compound 3

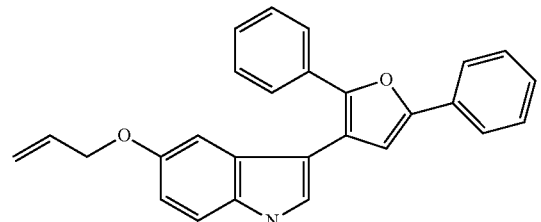

5-(allyloxy)-3-(2, 5-diphenylfuran-3-yl)-1H-indole

-continued

Compound 4

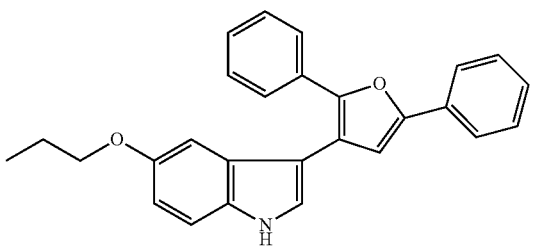

3-(2, 5-diphenylfuran-3-yl)-5-propoxy-1H-indole

Compound 5

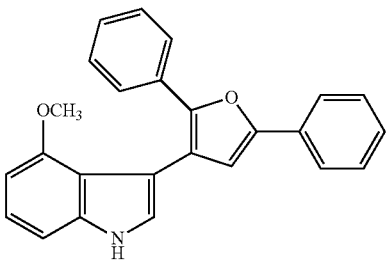

4-methoxy-3-(2, 5-diphenylfuran-3-yl)-1H-indole

Compound 6

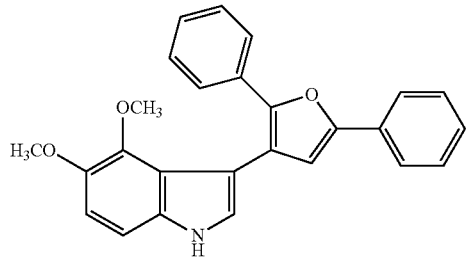

4,5-dimethoxy-3-(2,5-diphenylfuran-3-yl)-1H-indole

Compound 7

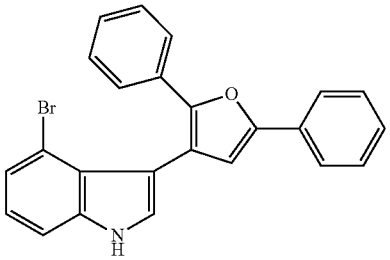

4-bromo-3-(2, 5-diphenylfuran-3-yl)-1H-indole

Compound 8

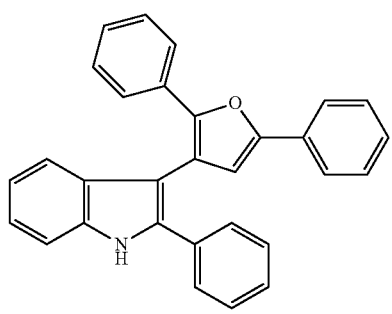

2-phenyl-3-(2, 5-diphenylfuran-3-yl)-1H-indole

Compound 9

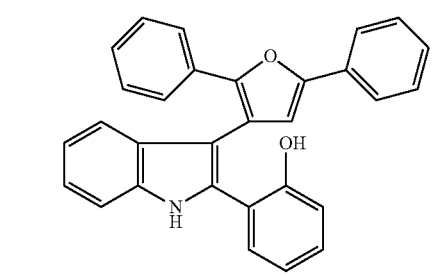

3-(2,5-diphenylfuran-3-yl)-2-(2-hydroxyphenyl)-1H-indole

Compound 10

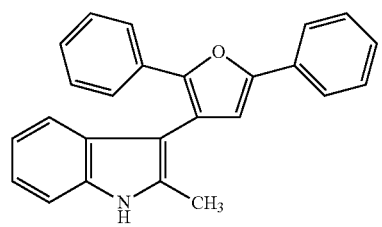

2-methyl-3-(2,5-diphenylfuran-3-yl)-1H-indole

Compound 11

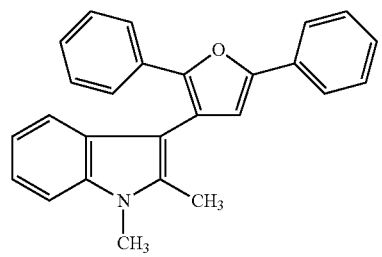

1,2-dimethyl-3-(2,5-diphenylfuran-3-yl)-1H-indole

Compound 12

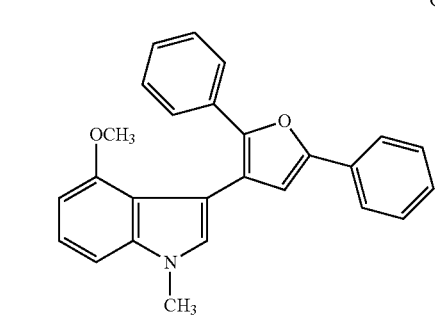

4-methoxy-1-methyl-3-(2, 5-diphenylfuran-3-yl)-1H-indole

Compound 13

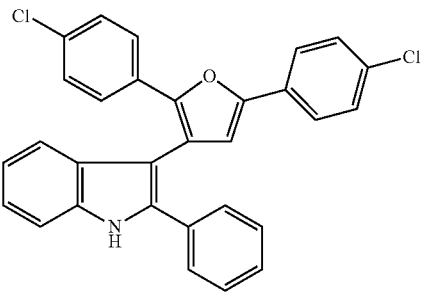

3-[2, 5-bis(4-chlorophenyl)furan-3-yl]-2-phenyl-1H-indole

Compound 14

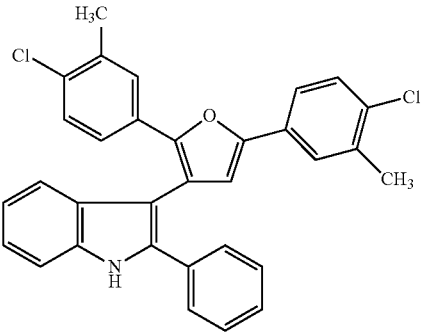

3-[2, 5-bis(4-chloro-3-methylphenyl)furan-3-yl]-2-phenyl-1H-indole

Compound 15

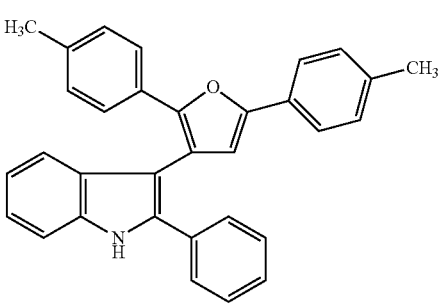

2-phenyl-3-(2, 5-di-p-tolylfuran-3-yl)-1H-indole

Compound 16

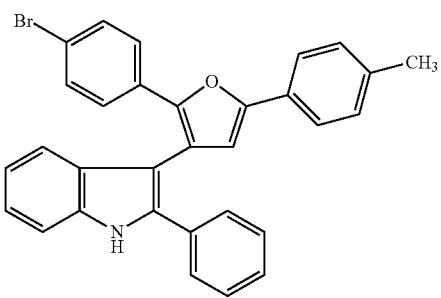

3-[2,5-bis(4-bromophenyl)furan-3-yl]-2-phenyl-1H-indole

EXAMPLES

The following examples are given by way of illustration of the present invention and therefore should not be construed to limit the scope of the present invention.

Example 1—Optimization of Lead Molecule for Detailed Mechanistic & Gastric Inflammatory Studies The anti-ulcer efficacy of compound 1, 3-(2,5-diphenyl-furan-3-yl)-1H-indol-5-ol showed 78% efficacy when administered orally (table 2). However, despite the presence of a common indole scaffold, compound 1, the potency of each compound is influenced by the nature of the substituent group present in it. Initially, the inventors investigated the effects of substitution around the indole skeleton so as to get better activity than compound 1 against ulcer. Incorporation of $OCH_3$ at C-5 of indole ring (compound 2) indeed resulted in 83% inhibition in ulcer index under oral administration (Table 2).

Figure 2A:
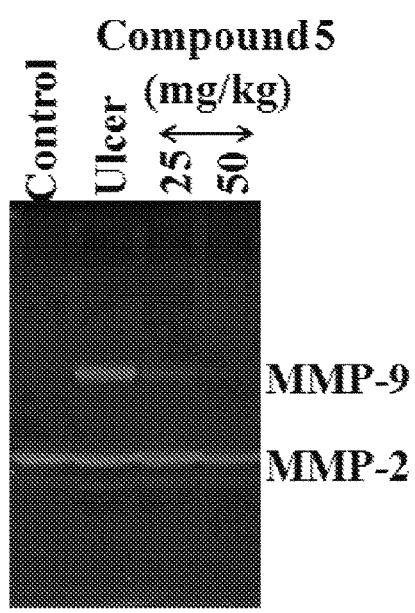
FIG. 2A depicts compound 5 inhibits MMP-9 activity in gastric mucosa Gelatin zymography for the assessment of MMP-9 activity in gastric tissue extracts of mice from ulcerated and compound 5 treated group.

The inventors were further interested to find out the outcome when 5-hydroxy oxygen of compound 1 was protected with different alkyl chains. However, moderate anti-ulcer efficacy was observed in vitro for 5-allyloxy (compound 3) and 5-propoxy (compound 4) substituted 3-furanyl indoles. In order to understand the substituent effect over indole 4-position, it was further screened with 4-methoxy and 4-bromo substituted 3-furanyl indoles, compound 5 and 7 respectively. Supported from the in vitro analysis, the most optimised effect was obtained upon modification of the indole 4-position with the incorporation of a methoxy group. 4-Methoxy-3-(2,5-diphenylfuran-3-yl)-1H-indole, compound 5 responded an interestingly higher ulcer inhibitory activity (95%) under oral administration (Table 2). The inventors also reasoned through in vitro analysis that addition of a non-hydrogen group such as methyl on indole nitrogen (compound 11 and 12) is not acceptable to have good anti-ulcer activity. The results demonstrate that indole NH plays a significant role in reducing the ulcer efficacy significantly. Among all new 3-indolyl furanoids, compound 5 exhibited significantly higher ulcer inhibitory activity in vivo as well as inhibition of MMP-9 activity (Table 2, FIG. 2). It was pertinent to mention that m and p-substituents on phenyl rings of furanyl group with methyl, chlorine or bromine (compound 13-16) exhibited lower anti-ulcer activity against MMP-9. From these results, it was revealed that methoxy group either at 4-position or 5-position of indole ring of new structurally proposed 3-furanyl indoles exhibited the most potent anti-ulcer property through inhibition of MMP-9 activities both in vitro and in vivo. Notably, when the substituents around indole were 4,5-dimethoxy, compound 6, the anti-ulcer activity was remarkably low (74% inhibitory effect). In particular, compound 5 exhibited the most promising optimised molecule for the treatment of gastric ulcer and other inflammatory diseases (table 2). Thus, compound 5 was chosen as lead molecule for further study.

Example 2

Column chromatography was carried out using silica gel 100-200 mesh. Analytical thin-layer chromatography (TLC) was performed with silica gel 60 $F_{254}$ aluminium sheets. $^1H$ NMR spectra were recorded on a Bruker DPX 300 MHz or Bruker DRX 600 MHz NMR instrument at ambient temperature in $CDCl_3$, $CD_3OD$ or DMSO-$d_6$. $^{13}C$ NMR spectra were recorded at 75 MHz or 150 MHz at ambient temperature. The chemical shifts were recorded in parts per million (ppm) with TMS as internal reference. All $^{13}C$ NMR spectra were recorded with complete proton decoupling. Mass spectral data refer to EIMS or ESIMS and are recorded in m/z unit. DI-EIMS were recorded on a GC-MS Shimadzu-QP5050A and ESIMS were done on a Waters® Micromass® Q-TOF Mass Spectrometer. Melting points are recorded on a SPAC-N SERVICE (India) melting point apparatus (Laboratory device) in open capillaries and are uncorrected. Elemental analyses were performed by Perkin-Elmer CHN/O analyzer model 2400, series II. HPLC analysis of plasma samples were performed on a Shimadzu Model SPD-M10Avp equipped with LC-10ATvp HPLC pump, Hamamatsu Deuterium Lamp type L6585 photodiode array detector. Chromatography was achieved using a Phenomenex Luna 5 μm C18 (2) 100 Å LC Column (150×4.6 mm I. D.) with Guard Cartridges C18 (4×3.0 mm). The mobile phase consisted of 15% water in acetonitrile, and solutes were eluted using a flow rate 1.0 mL/min. The column was re-equilibrated at initial conditions for 5 min before the next analysis. Analytical HPLC conditions were as follows: column, Pheomenex C18 (250 mm×4.6 mm, particle size 5 μm) with solvent combination of 0.5-1.0% TFA in water:acetonitrile in various ratios at a flow rate of 0.5-1.0 mL/min, detection at 254 nm. Purity of tested compounds was established by analytical reverse phase HPLC, confirming a purity of at least 95%. Unless otherwise stated, reagents were procured from commercial sources and were used without further purification.

Example 3—General Procedure for Preparation of 3-Indolyl Furanoids (Compound 1, 2, 5, and 7-16)

To a stirring solution of trans-1,2-dibenzoyl ethylene (2a, 236 mg, 1 mmol) in DCM (5 mL) under argon, 2-phenyl indole (193 mg, 1 mmol) and 5 mol % of p-TsOH (9.5 mg) were added. The reaction mixture was refluxed for 1 h at 40° C. The progress of reaction was monitored by thin layer chromatography with solvent system 1:1 chloroform/pet-ether. After completion of the reaction, the organic material was extracted with ethyl acetate (3×20 mL). The organic phase was dried over anhydrous sodium sulphate and concentrated at reduced pressure to produce a solid mass. Column chromatography of the residue over silica gel using increasing concentration of chloroform in petroleum ether eluted compound 8 as pink solid (349 mg, 85%).

Example 4—Procedure for Synthesis of Compounds 3 and 4

3-(2,5-Diphenylfuran-3-yl)-1H-indol-5-ol (compound 1) was synthesized according to the above mentioned procedure. To a stirring solution of compound 1 (200 mg, 0.569 mmol) in DMF (1 mL) was added cesium carbonate (222 mg, 0.682 mmol), stirred for 30 min at room temperature and allyl bromide (74 μL, 0.853 mmol) was added. The progress of reaction was monitored by thin layer chromatography with mobile phase 20% ethyl acetate in hexane. After 5-6 h of stirring at room temperature, it was washed with water and saturated ammonium chloride, and extracted with ethyl acetate (3×20 mL). The combined organic layers were washed with brine, dried over anhydrous sodium sulphate and evaporated to dryness under reduced pressure. Further purification by flash chromatography with 2% ethyl acetate in hexane as eluent provided the desired product 5-(allyloxy)-3-(2,5-diphenylfuran-3-yl)-1H-indole (compound 3) as light brown solid (163 mg, 73%).

Compound 4 (139 mg, 62% as dark brown solid) was prepared from compound 1 (200 mg, 0.569 mmol) following above mentioned reaction procedure where n-propyl bromide (78 μL, 0.853 mmol) was used as an alkylating agent.

Example 5—Procedure for Synthesis of Compound 6

Step-I:

To a stirring solution of 2,3-dihydroxy benzaldehyde (138 mg, 1 mmol) in acetone (10 mL) was added potassium carbonate (345 mg, 2.5 mmol). After 30 min of stirring at room temperature, dimethyl sulphate (237 μL, 2.5 mmol) was added dropwise and stirring was continued for further 5 h. Acetone was evaporated from the reaction mixture. The residue was washed with water, and extracted with diethyl ether (3×20 mL). The combined organic layers were washed with brine, dried over anhydrous sodium sulphate and evaporated to dryness under reduced pressure. Further purification by flash chromatography with 0.5-1% ethyl acetate in hexane provided the desired product 2,3-dimethoxy benzaldehyde as off-white solid (148 mg, 89%).

Step-II:

To a stirring solution of 2,3-dimethoxy benzaldehyde (166 mg, 1 mmol) in glacial acetic acid (3.3 mL) was added fuming nitric acid (790 μL). After 60 min of stirring at room temperature, the reaction mass was slowly poured into crushed ice. A heavy golden glow precipitation observed. The precipitate was filtered, washed with cold water, and then dried. The crude mixture of 5- and 6-nitro isomers were separated by flash chromatography with 12-16% ethyl acetate in hexane provided the desired product 2,3-dimethoxy 6-nitro benzaldehyde as pale yellow solid (93 mg, 44%) along with 2,3-dimethoxy 5-nitro benzaldehyde as pale yellow solid (80 mg, 38%).

Step-III:

The 2,3-dimethoxy-6-nitrobenzaldehyde (175 mg, 0.83 mmol) was converted into the corresponding 2,3-dimethoxy-6,β-dinitrostyrene by refluxing with nitromethane (356 μL, 6.64 mmol) in the presence of glacial acetic acid (1.3 mL) and ammonium acetate (71 mg, 0.91 mmol) for 4 h. The reaction mixture was allowed to cool to room temperature. Crushed ice was added, a yellow precipitation appeared. The precipitate was filtered, washed with cold water, and then dried. The crude mixture was purified by flash chromatography with 18-19% ethyl acetate in hexane provided the desired product as pale yellow solid (130 mg, 62%).

Step-IV:

To a stirring solution of 2,3-dimethoxy-6,β-dinitrostyrene (500 mg, 1.96 mmol) in glacial acetic acid (20 mL), were added iron dust (660 mg, 11.76 mmol) and ammonium acetate (303 mg, 3.936 mmol) and refluxed for 5 h. The reaction mixture was allowed to cool to room temperature. The reaction mass was filtered through a pad of celite and washed with chloroform. The filtrate was washed with water and brine, dried over anhydrous $Na_2SO_4$ and evaporated to dryness under vacuum. The crude mixture was purified by flash chromatography with 11-12% ethyl acetate in hexane provided the desired product 4,5-dimethoxy indole as pale brown solid (166 mg, 48%).

Step-V:

p-TsOH was added to a stirring solution of 4,5-dimethoxy indole (166 mg, 0.937 mmol) and trans-1,2-dibenzoyl ethylene (221 mg, 0.937 mmol). The reaction mixture was then heated at 40° C. for 5 h. After completion of the reaction, it was diluted with chloroform and washed with water and brine. The organic layer was dried over anhydrous $Na_2SO_4$ and evaporated to dryness under vacuum. The crude mixture was purified by flash chromatography with 4-6% ethyl acetate in hexane provided the desired product 4,5-dimethoxy-3-(2,5-diphenylfuran-3-yl)-1H-indole (compound 6) as yellowish red solid (289 mg, 78%).

Example 6—Biological Experiments

Animal experiments were carried out using Balb/c mice (20-25 g). Animals were anesthetized with ketamine (12 mg/kg b.w.) prior to cervical dislocation. Control and experimental animals were fasted for 6 hr with free access to water.

Balb/c mice (20-25 g) bred in-house with free access to food and water was used for all experiments. Experiments were designed to minimize animal suffering and to use the minimum number associated with valid statistical evaluation. Animals were anesthetized with ketamine (12 mg/kg b.w.) followed by cervical dislocation. Animal experiments were carried out following the guidelines of animal ethics committee of the institute. Control and experimental animals were fasted for 6 h with free access to water.

Protection Studies of Gastric Ulceration In Vivo

Before ulcer induction, animals of both control and experimental groups were kept separately in standard controlled conditions. Acute gastric ulcers were induced by oral administration of indomethacin at a dose of 80 mg/kg b.w. The control group received the vehicle only (olive oil), whereas the experimental group received indomethacin for gastric ulceration. After 4 h, the animals were sacrificed and gastric lesions in the fundic stomach were scored and expressed as obtained by counting the number of red bands/dots as follows: 0=no pathology; 1=a small pinhead ulcer spot; and 2-5=a band like lesion of 2-5 mm length. Total score become ~50 when ulcer is severe. The sum of the total scores as divided by the number of animals was expressed as the mean ulcer index. Formulations were administered orally 30 min prior to indomethacin treatment to check the gastroprotective effect. Among all the chemical compositions of 3-indolyl furanoids synthesized (table 1), compounds 1, 2, 5, 8, 9 and 12 were tested for prevention studies against gastric inflammation in vivo. Ulcer indices for animals treated with the selected synthetic compositions are presented in table 2. The results show that compound 5 is the optimised chemical composition having most promising antiulcer activity for further studies.

TABLE 2

Anti-ulcer efficacy of 3-indolyl furanoids under oral administration

| Group | Treatment | Dose (mg/kg body weight)$^a$ | Mean Ulcer Index ± SEM$^b$ | Inhibition of Ulceration (%)$^c$ |
|---|---|---|---|---|
| 1 | Vehicle | olive oil | 0.5 ± 0.5 | 98 |
|   |   |   |   | no effect |
| 2 | Indomethacin (Ulcer) | 80 | 52.5 ± 1.4 | 1000 |
| 3 | Omeprazole | 12 | 0.5 ± 0.5 | 100 |
| 4 | compound 1 | 50 | 11.5 ± 2.25 | 78 |
| 5 | compound 2 | 50 | 9 ± 2.4 | 83 |
| 6 | compound 3 | 50 | n.d. | n.d. |
| 7 | compound 4 | 50 | n.d. | n.d. |
| 8 | compound 5 | 50 | 2.5 ± 0.86 | 95 |
| 9 | compound 6 | 50 | 13.5 ± 1.25 | 74 |
| 10 | compound 7 | 50 | n.d. | n.d. |
| 11 | compound 8 | 50 | 18.25 ± 4.25 | 65 |
| 12 | compound 9 | 50 | 14.5 ± 2.1 | 72 |
| 13 | compound 10 | 50 | n.d. | n.d. |
| 14 | compound 11 | 50 | n.d. | n.d. |
| 15 | compound 12 | 50 | 23.25 ± 1.25 | 56 |
| 16 | compound 13 | 50 | n.d. | n.d. |
| 17 | compound 14 | 50 | n.d. | n.d. |

TABLE 2-continued

Anti-ulcer efficacy of 3-indolyl furanoids under oral administration

| Group | Treatment | Dose (mg/kg body weight)[a] | Mean Ulcer Index ± SEM[b] | Inhibition of Ulceration (%)[c] |
|---|---|---|---|---|
| 18 | compound 15 | 50 | n.d. | n.d. |
| 19 | compound 16 | 50 | n.d. | n.d. |

[a]Each Balb/c mice received indomethacin at a dose of 80 mg/kg b.w. 30 min prior treatment by chemical compositions of general formula 1 (compounds 1, 2, 5, 8, 9 and 12) at a dose of 50 mg/kg bw. All compounds were dissolved in olive oil.
[b]Not determined.
[c]Percentage inhibition of ulceration was calculated by unitary method considering indomethacin caused 100% ulceration.

Figure 1B:
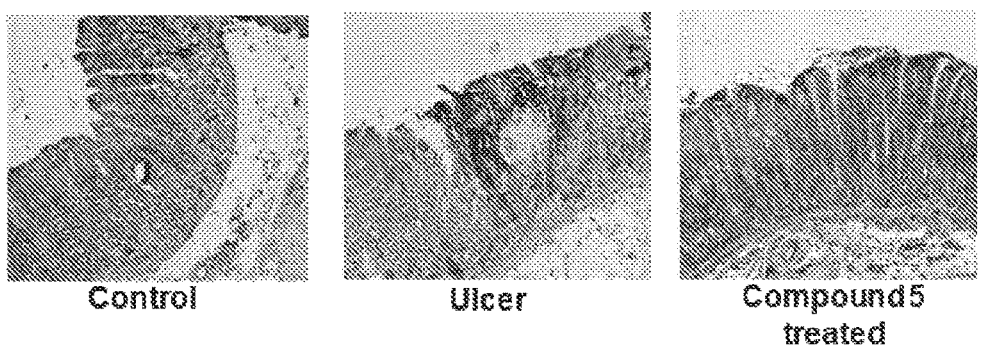

Assessment of Overall Inflammation in Indifferent Layers of Gastric Tissue in Mouse from Normal, Ulcerated and Compound 5 Treated Groups Histological Studies, and TUNEL Assay To understand the fine information about the physical condition (the level of damage and/or intactness) of cells tissues under observation, different tissue samples were fixed in 10% formalin and embedded in paraffin. Tissue sections were deparaffinized with xylene and rehydrated with descending alcohol series. The sections were cut using microtome, and stained with hematoxylin and eosin, or subjected to Terminal deoxynucleotidyl transferase-mediated dUTP Nick End Labeling (TUNEL) assay by using a in situ apoptosis detection kit. Fixation, permeabilization, and staining were carried out in exact parallel to ensure comparative significance among normal, ulcerated and compound 5 treated groups. Haematoxylin-eosin staining of gastric tissue sections of gastric epithelium and submucosa in control, ulcerated, and compound 5 treated tissues revealed disruption and exfoliation of the gastric epithelial layer during ulceration in comparison to that of control, while in compound 5 treated mice (50 mg/kg body weight) gastric tissues displayed minimum injury and intact epithelial layer (FIG. 1A). In addition, the terminal deoxynucleotidyl transferase-mediated dUTP nick end labelling (TUNEL) assay showed suppression of apoptosis of gastric mucosa of ulcerated mice by synthetically prepared compound 5. The images were observed in an Olympus microscope. Images at 10× and 40× magnification were captured using Camedia software (E-20P 5.0 Megapixel) and processed under Adobe Photoshop version 7.0 (FIG. 1B).

Histological Studies, TUNEL Assay and Immunofluorescence

Tissue sections were stained with hematoxylin and eosin stain. Fixation, permeabilization, and staining were carried out in parallel in normal, ulcerated and compound 5 treated groups to ensure comparative significance among different treatment. TUNEL assay is used for detection and quantification of apoptosis in gastric tissues, based on labelling of DNA strand breaks. Terminal deoxynucleotidyl transferase-mediated dUTP Nick End Labeling (TUNEL) assay was performed by using an in situ apoptosis detection kit. For immunofluorescence study, antigen retrieval was performed by trypsin (0.05% trypsin, 0.1% $CaCl_2$) and blocking was performed using 5% BSA in Tris Buffered Saline (20 mM Tris-HCl, pH 7.4 containing 150 mM NaCl) followed by incubation in primary antibody (MMP-9 polyclonal) solution, followed by FITC-conjugated secondary antibody.

Measurement of Oxidative Stress (Protein Carbonyl, Lipid Peroxidation) in Normal, Ulcerated and Compound 5 Treated Mice Measurement of Protein Carbonyl Protein carbonyl groups are considered as biomarkers of oxidative stress. Protein oxidation was measured as carbonyl content in the low speed supernatant of the gastric tissue homogenate. The stomach from control, stress ulcerated, and compound 5 treated (50 mg/kg bw) mice were homogenized in 50 mM sodium phosphate buffer pH 7.4 in a Potter-Elvehjem glass homogenizer for 2 min to get 20% homogenate. After centrifugation at 600 g for 10 min, the proteins from 1.0 mL of the supernatant were precipitated with 10% trichloroacetic acid and allowed to react with 0.5 mL of 10 mM 2,4-dinitrophenyl hydrazine for 1 h. After precipitation with 20% trichloroacetic acid, proteins were washed thrice with a mixture of ethanol-ethyl acetate (1:1), dissolved in 1.0 mL of a solution containing 6 M guanidine HCl in 20 mM potassium phosphate adjusted to pH 2.3 with trifluoroacetic acid, and centrifuged. The absorbance of the supernatant was read at 362 nm for carbonyl content (E=22,000/M/cm). The ulcerated group showed 3.49±0.47 nmol/mg protein compared to 0.98±0.21 nmol/mg protein for the non-ulcerated group, while compound 5 treatment showed very good reduction (1.58±0.18 nmol/mg) in protein content (Table 3).

The fundic stomach homogenate was used for measurement of protein carbonyl formation as nmol/mg protein.

Measurement of Lipid Peroxidation

The fundic stomach homogenate was used for measurement of lipid peroxide content as thiobarbituric acid reactive species (TBARS).

Measurement of Lipid Peroxidation

The cytosolic fraction from the gastric tissue homogenate was used for measurement of lipid peroxide content as thiobarbituric acid reactive species (TBARS). Briefly, 1 mL of the cytosolic fraction was allowed to react with 2 mL of TCA-TBA-HCl (15% TCA, 0.375% TBA, 0.25 N HCl) reagent, heated in a boiling water-bath for 15 min, cooled and centrifuged. The absorbance of the supernatant was measured for nano moles of TBARS at 535 nm ($\varepsilon=1.5\times10^5$/M/cm). Ulcerated group showed 1.40±0.03 nmol TBARS/mg tissue compared to 0.41±0.04 nmol TBARS/mg tissue for non ulcerated group, while compound 5 treatment showed very good reduction of nmol TBARS/mg tissue to 0.47±0.15 (Table 3).

Measurement of In Vivo Anti-Inflammatory Property of Compound 5

Myeloperoxidase Assay

To understand the anti-inflammatory activity of compound 5, the inventors performed Myeloperoxidase (MPO) Assay in mouse of control, diseased and treated. Myeloperoxidase (MPO) activity in the mice gastric tissues was measured by calorimetric assay using guaiacol as the substrate. Briefly, gastric tissue homogenate prepared in 5 mM phosphate buffer was added to 1 mL of reaction buffer containing 0.5 mM $H_2O_2$ and 0.4 M guaiacol in 50 mM phosphate buffer, pH 7.4. The changes in the optical density per minute for tetraguaiacol were measured at 470 nm in a Shimadzu spectrophotometer. The results were expressed in units/gram gastric tissue ($\varepsilon=26.6$/mM/cm). The ulcerated group showed 34.60±0.13 units/gram tissue compared to 5.16±0.51 units/gram tissue for non ulcerated group, while compound 5 treatment showed very good reduction in units/gram tissue to 9.13±0.33 (Table 3).

TABLE 3

Anti-oxidative and anti-inflammatory activity of compound 5 during gastroprotection

| Assays | Control | Ulcer | Compound 5 treated |
|---|---|---|---|
| Protein carbonylation (nmol/mg protein) | 0.98 ± 0.21 | 3.49 ± 0.47 | 1.58 ± 0.18 |
| Lipid peroxidation (nmol TBARS/mg tissue) | 0.41 ± 0.04 | 1.40 ± 0.03 | 0.47 ± 0.15 |
| Myeloperoxidase (units/gram tissue) | 5.16 ± 0.51 | 34.60 ± 0.13 | 9.13 ± 0.33 |

Myeloperoxidase Assay

Myeloperoxidase (MPO) activity in the mouse gastric tissue homogenate was assayed colorimetrically using guaiacol and $H_2O_2$.

Assessment of MMP-9 Activity in Gastric Tissue Extract

Tissue Extraction

The whole stomach (including fundic, body and pyloric parts) was washed with saline and used for extraction. Stomach except connective tissue layer (named as gastric tissue) were suspended in 10 mM phosphate buffer saline (PBS) containing protease inhibitors, minced and incubated for 10 min at 4° C. After centrifugation at 12,000 g for 15 min, the supernatant was collected as PBS extracts. The pellet was then extracted in lysis buffer (10 mM Tris-HCl pH 8.0, 150 mM NaCl, 1% Triton X-100 and protease inhibitors) and centrifuged at 12,000 g for 15 min to obtain TX extracts. Both PBS and TX extracts were preserved at −70° C. and used in future studies. Proteins were estimated either by Lowry method or by Bradford assay.

Gelatin Zymography for Assessment of MMP-9 Activity in Gastric Tissue Extract

For the analysis of MMP-9 activity, tissue extracts were electrophoresed in 8% SDS-PAGE containing 1 mg/mL gelatin under nonreducing conditions. Equal amounts of tissue extracts (70 µg of total protein) were loaded in all the lanes. The gels were washed twice in 2.5% Triton X-100 and then incubated in calcium assay buffer (40 mm Tris-HCl, pH 7.4, 0.2 M NaCl, 10 mM $CaCl_2$) for 18 hr at 37° C. Gels were stained with 0.1% Coomassie blue followed by destaining. The zones of gelatinolytic activity came as negative staining. Quantification of zymographic bands was performed using densitometry linked to proper software (Lab Image, Kapelan Gmbh, Leipzig, Germany).

Figure 2B:
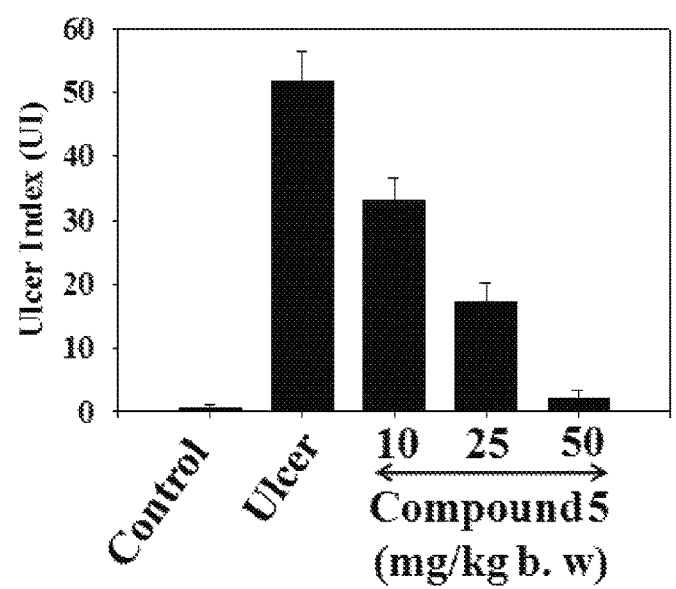
FIG. 2B is a bar graph of varying doses of compound 5 that were administered orally to each group of mice prior to indomethacin (80 mg/kg) treatment. Animals were sacrificed after 4 h, and the ulcer indices were scored.

This study was aimed at determining the regulation of MMP-9 activity in indomethacin-induced acute gastric ulceration. Indomethacin ulcerated stomach extracts (FIG. 2A) exhibit significant upregulation of pro-MMP-9 (92 kDa), while compound 5 pretreatment dose dependently showed inhibition of that protease in gastric milieu which strongly correlated with ulcer indices data (FIG. 2B). Therefore there is a significant correlation between MMP-9 down regulation and antiulcer efficacy of compound 5. Compound 5 inhibited MMP-9 activity very significantly while MMP-2 activity remained unaltered. 10 mg/kg bw compound 5 showed 40% and 25 mg/kg bw showed 80% inhibition in ulcer index (FIG. 2B).

The whole stomach was washed with saline and suspended in 10 mM phosphate buffer saline (PBS) containing protease inhibitors, minced, and incubated for 10 min at 4° C. After centrifugation at 12,000 g for 15 min, the supernatant was collected as PBS extracts. The pellet was then extracted in lysis buffer (10 mM Tris-HCl pH 8.0, 150 mM NaCl, and 1% Triton X-100 and protease inhibitors) and centrifuged at 12,000 g for 15 min to obtain TX extracts. Both PBS and TX extracts were preserved at −70° C. and used in future studies. Proteins were estimated either by Lowry method or by Bradford assay.

Gelatin Zymography

Tissue extracts were electrophoresed in SDS-PAGE containing gelatin under nonreducing conditions. The gels were washed in 2.5% Triton X-100, then incubated in calcium assay buffer and subjected to staining by Coomassie blue. Gelatinolytic activity came as negative staining and was quantified by Lab Image software.

Purification of MMP-9 from Bronchoalveolar Lavage Fluids (BALF)

MMP-9 was purified from the bronchoalveolar lavage fluid (BALF) of idiopathic pulmonary fibrosis (IPF) patients as these fluids contain enormous amounts of MMP-9. All purification procedures were carried out at 4° C. Briefly, BALF containing protease inhibitor cocktail (EDTA Free) were centrifuged at 12,000 g for 15 min, and the supernatant was collected and processed for protein purification. The protein was purified by affinity chromatography on a gelatin-Agarose (Sigma-G5384) column equilibrated with 50 mM Tris-HCl, pH 7.5, 150 mM NaCl, 5 mM $CaCl_2$ and 0.02% Brij-35. The enzyme was eluted with 7% dimethyl sulfoxide diluted in the same buffer, and the fractions containing enzyme protein as determined by absorbance at 280 nm were pooled and immediately dialyzed against equilibrating buffer at 4° C. They were then concentrated using Amicon Ultra-15 centrifugal filter devices and protein concentration was determined by Bradford assay. These samples were screened to confirm the presence of MMP-9 and absence of MMP-2 by gelatin zymography and stored at −70° C.

Figure 3:
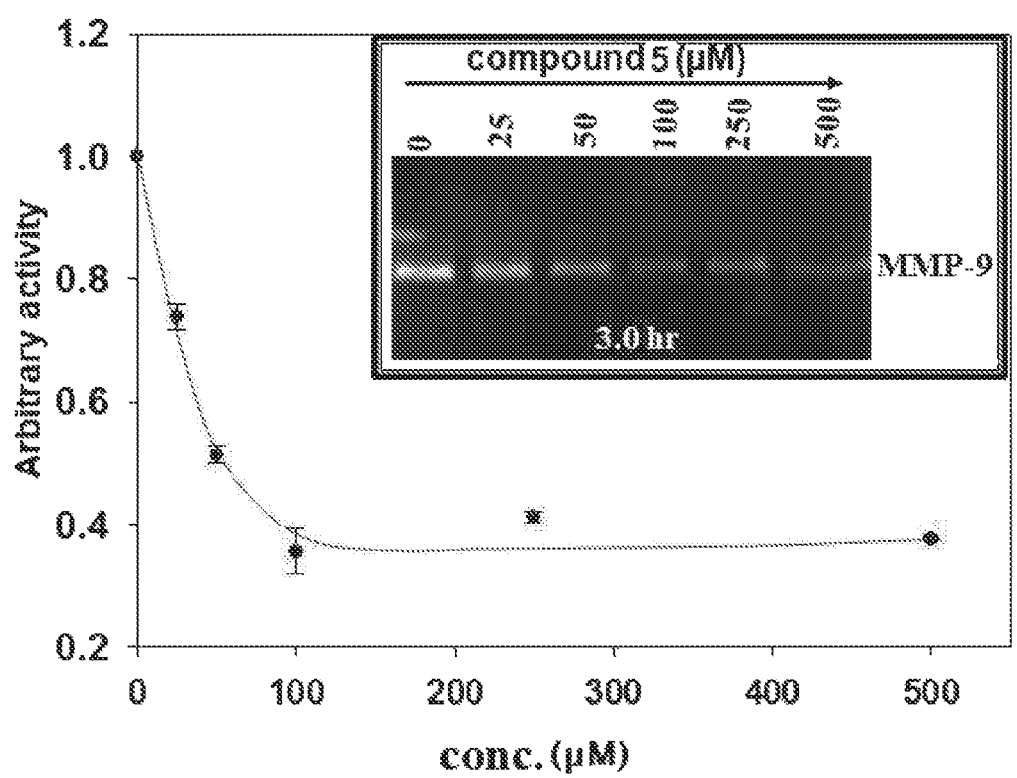
FIG. 3 shows the determination of the half-maximal inhibitory concentration ($IC_{50}$) of compound 5 using gelatin zymography.

Determination of the Half-Maximal Inhibitory Concentration ($IC_{50}$) of Compound 5 Using Gelatin Zymography The inventors address the $IC_{50}$ value of compound 5 towards MMP-9 binding. To evaluate the $IC_{50}$ value of compound 5 on MMP-9 activity, equal amount of purified MMP-9 was incubated with various concentrations of compound 5 followed by electrophoresis in 8% SDS-PAGE containing 1 mg/mL gelatin under nonreducing conditions. Band intensities were calculated from three independent experiments and were plotted against the dose of compound 5 and $IC_{50}$ value was found to be ~50 µM. Inset shows the substrate gel (FIG. 3).

Toxicity Studies Through Repeat Daily Dosing of Compound 5

Figure 4:
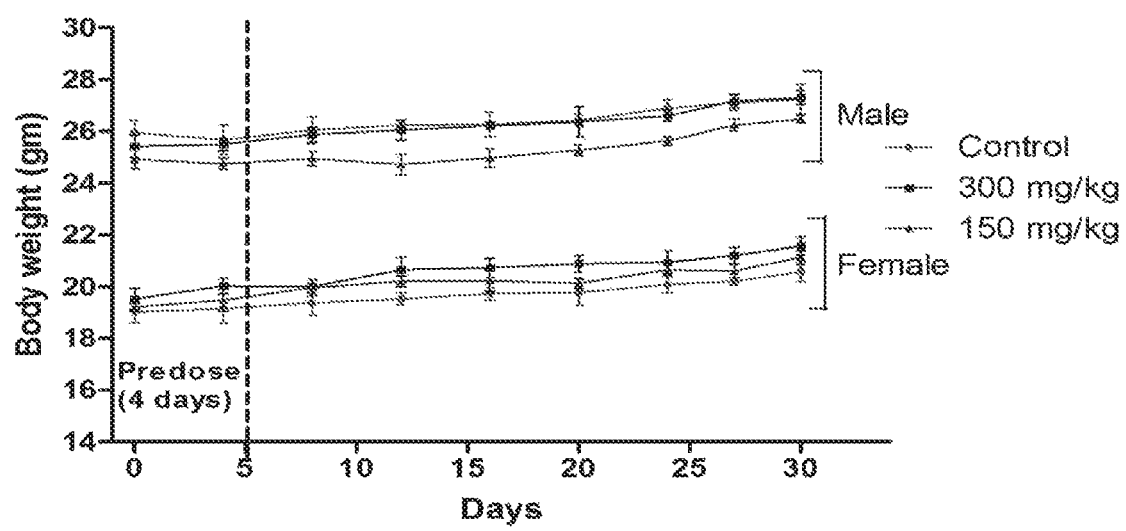
FIG. 4 gives the In vivo toxicity test. Male and female BALB/c mice (n=10) received indicated doses of compound 5 by daily gavage. Control mice received vehicle (olive oil). Body weights were determined 4 days before the start of the treatment and then throughout the period of treatment until day 25. Data points represent mean body weight.

The purpose of this study was to assess the efficacy of prolonged oral compound 5 treatment and ascertaining adverse impact, if any. Throughout the period of treatment, the inventors found no mortality and no clinical signs of toxicity (lethargy, abdominal distension, fur loss, hunching) at the tested doses of compound 5 (150 or 300 mg/kg body weight/day for 25 days). The female mice were, on an average, 4 g lighter than male mice which is consistent with the common sex-specific weight difference. There were no differences in body weight between the treated and control groups (FIG. 4).

Pharmacokinetic Profiling of Compound 5 in Rat

Figure 5:
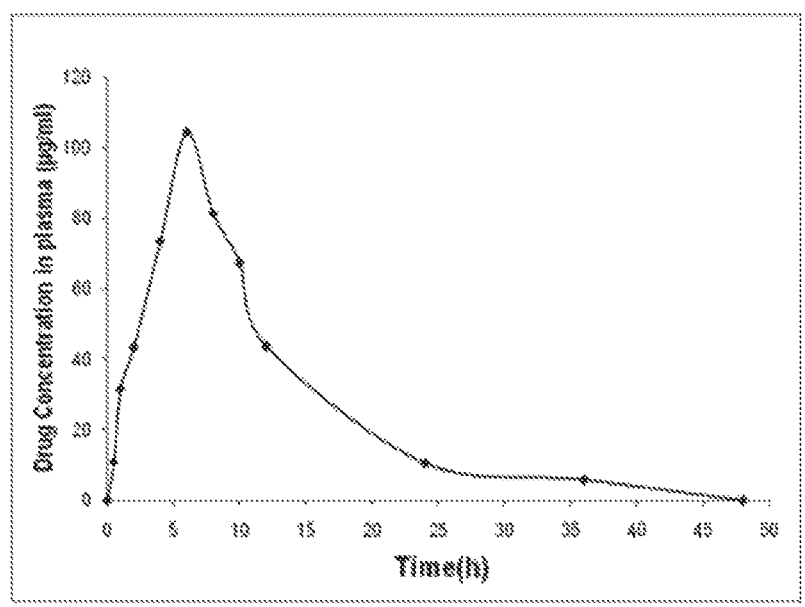
FIG. 5 shows the Pharmacokinetic profile of compound 5. Male sprague dawley rats (n=6) received a single dose of 250 mg/kg body weight compound 5 by oral gavage. Compound 5 levels in plasma were determined by HPLC. Values represent mean plasma levels.
Figure 6:
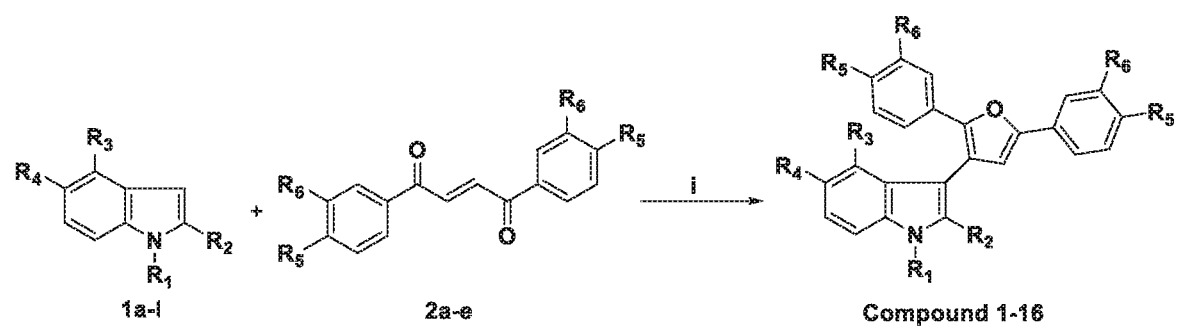
FIG. 6 shows Scheme 1, the synthetic route for the targeted, 3-indolyl furanoid derivatives giving reagents and condition: (i) p-TsOH (0.5 equiv.), CH2C12, 1-6 h, reflux.
Figure 7:
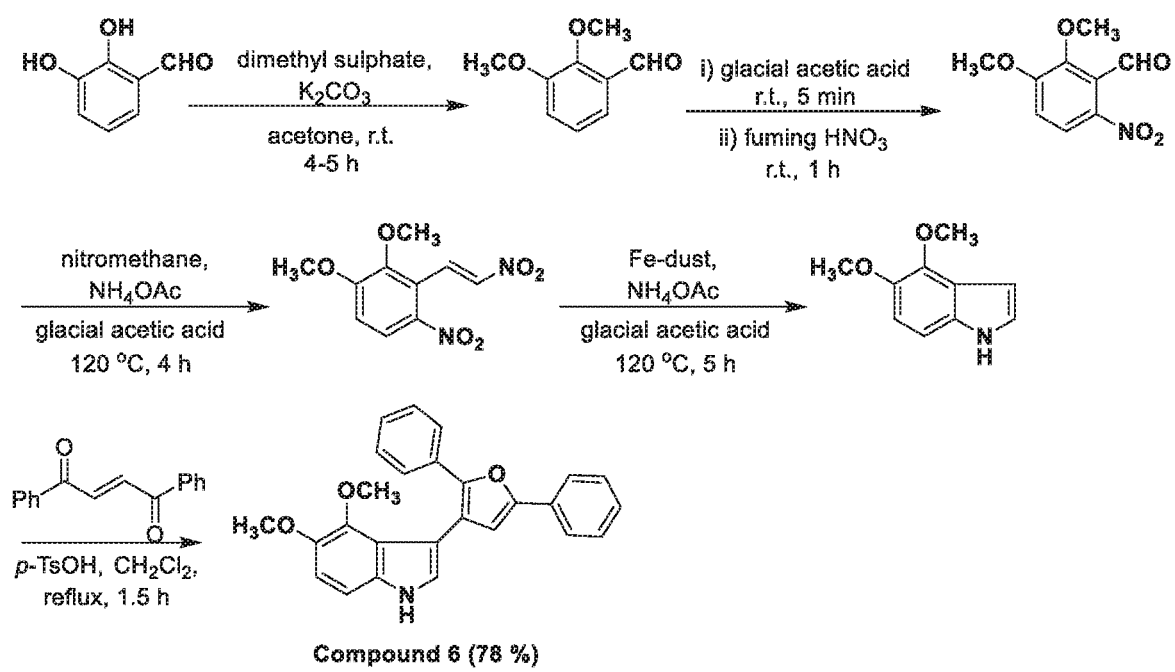
FIG. 7 shows Scheme 2, the synthetic route for 4,5-dimethoxy-3-(2,5-diphenylfuran-3-yl)-1H-indole (compound 6).

In order to assess the time course of action and disposition of compound 5 in vivo, pharmacokinetic studies in Sprague Dawley rats were conducted. The mean concentration-time profile in the plasma samples for compound 5 is shown in FIG. 5. The curve was linear in the range investigated and the extraction efficiency was greater than 70%. It shows a gradual rise in drug concentration to a maximum value ($C_{max}$=104.48 µg/mL) at approximately 6.0 h ($t_{max}$) after treatment, followed by a polyexponential decline with a relatively long terminal phase, half-life and area under the curve being 7.0 h and 1273.8 h μg/mL respectively.

Various Noted Advantages

Embodiments of the present invention involve development of new 3-indolyl furanoids of formula 1 for treatment of gastric ulcer and other inflammatory diseases. The formulation of compound 5 is found to have potent anti-inflammatory activity and anti-ulcer activity with $IC_{50}$ value of 50 μM.

All the studied new molecules of general formula 1 are feasible to synthesize in large scales with good yields from easily available starting materials. Therefore commercialization of this invention can be cost effective which reflects its patentability.

Better activity of 3-indolyl furanoids also opens the scope for the development of translational medicine in the field of drug discovery.

Embodiments of the present invention have the following noted advantages, and not limited thereto, with respect to commercialization:
(1) Utilization in Biotech. Industry
(2) Utilization in Chemical Industry Embodiments of the invention are the perfect combination of synthetic chemistry and advanced biology to represent chemical biology for the prevention of gastric ulcer and other inflammatory diseases.

REFERENCES

1. *J. Biol. Chem.*, 2005, 280, 9409.
2. *Clin Med Res.*, 2007, 5, 19.
3. *J Int Oral Health.*, 2014, 6, 94.
4. *Mol. Ther.* 2014, 22, 69.
5. *J. Biol. Chem.*, 2008, 283, 20087.
6. *Bioinformation.*, 2011; 5, 310.
7. *Biochimica et Biophysica Acta.*, 2010, 1803, 29.
8. *Biochimica et Biophysica Acta.*, 2014, 1843, 603

What is claimed is:
1. A compound of formula 1

Formula 1

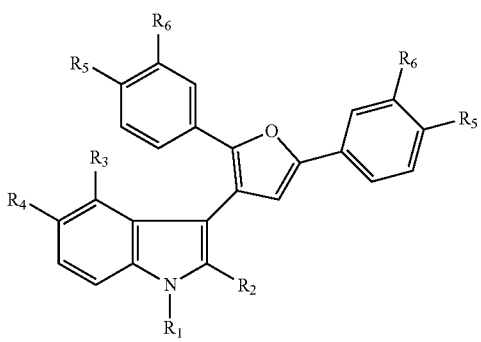

wherein
$R_1$ is H, OH, $OCH_3$, Br, Cl, Ph, o-$OHC_6H_4$, $OCH_2$—CH=$CH_2$, or $OCH_2CH_2CH_3$;
$R_2$ is H, OH, $OCH_3$, Br, Cl, Ph, o-$OHC_6H_4$, $OCH_2$—CH=$CH_2$, or $OCH_2CH_2CH_3$;
$R_3$ is H, OH, $OCH_3$, Br, Cl, Ph, o-$OHC_6H_4$, $OCH_2$—CH=$CH_2$, or $OCH_2CH_2CH_3$;
$R_4$ is H, OH, $OCH_3$, Br, Cl, Ph, o-$OHC_6H_4$, $OCH_2$—CH=$CH_2$, or $OCH_2CH_2CH_3$;
$R_5$ is H, OH, $OCH_3$, Br, Cl, Ph, o-$OHC_6H_4$, $OCH_2$—CH=$CH_2$, or $OCH_2CH_2CH_3$; and
$R_6$ is H, OH, $OCH_3$, Br, Cl, Ph or o-$OHC_6H_4$, $OCH_2$—CH=$CH_2$, or $OCH_2CH_2CH_3$;
wherein at least one of $R_1$, $R_2$, $R_3$, $R_4$, $R_5$ or $R_6$ is not H.

2. The compound selected from the group consisting of:
(1) 3-(2,5-diphenylfuran-3-yl)-1H-indol-5-ol;
(2) 3-(2,5-diphenylfuran-3-yl)-5-methoxy-1H-indole;
(3) 5-(allyloxy)-3-(2,5-diphenylfuran-3-yl)-1H-indole;
(4) 3-(2,5-diphenylfuran-3-yl)-5-propoxy-1H-indole;
(5) 4-methoxy-3-(2,5-diphenylfuran-3-yl)-1H-indole;
(6) 4,5-dimethoxy-3-(2,5-diphenylfuran-3-yl)-1H-indole;
(7) 4-bromo-3-(2,5-diphenylfuran-3-yl)-1H-indole;
(8) 2-phenyl-3-(2,5-diphenylfuran-3-yl)-1H-indole;
(9) 3-(2,5-diphenylfuran-3-yl)-2-(2-hydroxyphenyl)-1H-indole;
(12) 4-methoxy-1-methyl-3-(2,5-diphenylfuran-3-yl)-1H-indole;
(13) 3-[2,5-bis(4-chlorophenyl)furan-3-yl]-2-phenyl-1H-indole;
(14) 3-[2,5-bis(4-chloro-3-methylphenyl)furan-3-yl]-2-phenyl-1H-indole;
(15) 2-phenyl-3-(2,5-di-p-tolylfuran-3-yl)-1H-indole; and
(16) 3-[2,5-bis(4-bromophenyl)furan-3-yl]-2-phenyl-1H-indole.

3. A pharmaceutical composition comprising the compound of formula 1 according to claim 1 and pharmaceutically acceptable additives, wherein the compound is in the range of 0.1 to 99% of the pharmaceutical composition.

4. The pharmaceutical composition as claimed in claim 3, wherein the additives is selected from the group consisting of fillers, antioxidants, dispersants, emulsifiers, flavours, preservatives, solubilizers and colorants.

5. The pharmaceutical composition as claimed in claim 3, wherein the composition is in the form of tablets and capsules.

6. The pharmaceutical composition as claimed in claim 3, wherein the compound is in the range of 30 to 95% for tablets and 3-50% for capsules.

7. The pharmaceutical composition as claimed in claim 3, wherein $IC_{50}$ value for in vitro activity of compound of Formula 1 against AGS cells is ~50 M.

8. The pharmaceutical composition as claimed in claim 3, wherein said composition is administered through an oral route.

9. The pharmaceutical composition as claimed in claim 3, wherein said composition administered intraperitoneally.

10. The pharmaceutical composition as claimed in claim 3, wherein said composition is administered orally at a dose level ranging between 10 to 50 mg per kg body weight.

11. The pharmaceutical composition as claimed in claim 3, wherein said composition is administered intraperitoneally at a dose level ranging between 5 to 25 mg per kg body weight.

* * * * *